(12) United States Patent
Chou et al.

(10) Patent No.: US 8,580,731 B2
(45) Date of Patent: Nov. 12, 2013

(54) INSULIN-GOLD NANOCLUSTER, PHARMACEUTICAL COMPOSITION FOR REDUCING BLOOD GLUCOSE COMPRISING THE SAME, AND METHOD FOR DETECTING ADIPOSE CELLS IN TISSUE BY USING THE SAME

(75) Inventors: Pi-Tai Chou, Taipei (TW); Chien-Liang Liu, New Taipei (TW); Yun-Chen Chien, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/399,119

(22) Filed: Feb. 17, 2012

(65) Prior Publication Data

US 2013/0216588 A1 Aug. 22, 2013

(51) Int. Cl.
*A61K 38/28* (2006.01)
*C07K 14/62* (2006.01)

(52) U.S. Cl.
USPC ............................ 514/5.9; 514/21.4; 514/21.3

(58) Field of Classification Search
None
See application file for complete search history.

(56) References Cited

U.S. PATENT DOCUMENTS

2010/0273741 A1* 10/2010 Assaf .............................. 514/78
2011/0165689 A1 7/2011 Ying et al.

FOREIGN PATENT DOCUMENTS

WO  WO 2010016803 A1 * 2/2010
WO  WO 2010116185 A1 * 10/2010

OTHER PUBLICATIONS

Joshi et al., Gold Nanoparticles as Carriers for Efficient Transmucosal Insulin Delivery, Langmuir, vol. 22:300-305 (published online Dec. 3, 2005).*
Liu et al., Insulin-Directed Synthesis of Fluorescent Gold Nanoclusters: Preservation of Insulin Bioactivity and Versatility in Cell Imaging, Angew. Chem. Int. Ed. (Jun. 17, 2011), vol. 50:7056-7060.*
Chen-Zhong et al, Fluorescence properties of gold nanorods and their application for DNA biosensing, Chem. Commun., (2005) pp. 3924-3926.*
Yun-Chen Chien; Emitting Gold Nanodots Synthesized via Protein Templates; 2011 Taiwan International Science; Feb. 18, 2011.
Chien-Liang Liu, Hung-Tsung Wu, Yi-Hsuan Hsiao, Chih-Wei Lai, Chun-Wei Shih, Yung-Kang Peng, Kuo-Chun Tang, Hsing-Wei Chang, Yun-Chen Chien, Jong-Kai Hsiao, Juei-Tang Cheng and Pi-Tai Chou; Insulin-Directed Synthesis of Fluorescent Gold Nanoclusters: Preservation of Insulin Bioactivity and Versatility in Cell Imaging; Jun. 17, 2011, p. 7056-7060, Wiley.

* cited by examiner

*Primary Examiner* — Cecilia J Tsang
*Assistant Examiner* — Randall L Beane
(74) *Attorney, Agent, or Firm* — Bacon & Thomas, PLLC

(57) ABSTRACT

An insulin-gold nanocluster, a pharmaceutical composition for treating diabetes comprising the insulin-gold nanocluster, and a method for detecting adipose cells in a tissue by using the insulin-gold nanocluster are provided. Herein, the insulin-gold nanocluster of the present invention comprises: a gold nanocluster, and insulin connecting to the gold nanocluster, wherein the insulin-gold nanocluster emits red fluorescence at maximized wavelength of 670 nm.

10 Claims, 4 Drawing Sheets

INSULIN-GOLD NANOCLUSTER, PHARMACEUTICAL COMPOSITION FOR REDUCING BLOOD GLUCOSE COMPRISING THE SAME, AND METHOD FOR DETECTING ADIPOSE CELLS IN TISSUE BY USING THE SAME

BACKGROUND OF THE INVENTION

1. Field of the Invention

The present invention relates to an insulin-gold nanocluster, a pharmaceutical composition for treating diabetes comprising the insulin-gold nanocluster, and a method for detecting adipose cells in a tissue by using the insulin-gold nanocluster. More specifically, the present invention relates to a fluorescent insulin-gold nanocluster, a pharmaceutical composition for treating diabetes comprising the same, and a method for detecting adipose cells in a tissue by using the same.

2. Description of Related Art

Fluorescent nanomaterials and fluorescent nanoclusters have been developed and intensively studied, because of their unique optical and photophysical properties. In recent years, many studies discovered that fluorescent nanomaterials and fluorescent nanoclusters also have potential as replacement for conventional organic dyes in optical cell imaging. Among the various nanoclusters (NCs), gold nanoclusters are the most well studied due to their low toxicity and high biocompatibility.

Metal nanoclusters typically comprises several to tens metal atoms and the diameters thereof are generally in nanoscale, and especially about 1 nm. In addition, the nanoclusters are comparable to or smaller than the Fermi wavelength of conductive electrons, so the nanoclusters may carry quantum-mechanical properties to show promising signals on biomedical imaging.

Recently, some studies relating to Au nanoparticles encapsulated in certain enzymes have been reported. For example, US 2011/0165689 has been developed to synthesize gold nanoclusters with BSA, and the obtained BSA-gold nanoclusters can be applied to several devices, such as nanosensors of $Hg^{2+}$, $CN^-$ and $H_2O_2$. Although this patent has disclosed the protein-directed gold nanoclusters, there are few studies on bioactive protein-directed gold nanoclusters that can still preserve their own biological role.

Hence, it is desirable to provide bioactive protein-directed gold nanoclusters, for example, enzyme-directed gold nanoclusters, which still have biological activity. Therefore, the obtained bioactive protein-directed gold nanoclusters can be not only used as biosensors, but also applied to medical uses.

SUMMARY OF THE INVENTION

The object of the present invention is to provide an insulin-gold nanocluster and a method for manufacturing the same, wherein the insulin-gold nanocluster is capable of emitting red fluorescence.

Another object of the present invention is to provide a pharmaceutical composition comprising the aforementioned insulin-gold nanocluster, which can be applied to diabetes treatment.

A further object of the present invention is to provide a method for detecting adipose cells in a tissue by using the aforementioned insulin-gold nanocluster. In addition, this method can further be applied to evaluate a risk of diabetes on a subject.

To achieve the object, the insulin-gold nanocluster of the present invention comprises: a gold nanocluster, and insulin connecting to the gold nanocluster, wherein the insulin-gold nanocluster emits fluorescence at a wavelength between 620 nm and 690 nm.

The method for manufacturing the aforementioned insulin-gold nanocluster of the present invention comprises: providing a reaction mixture containing a gold precursor and insulin; reducing the gold precursor in the reaction mixture with the insulin at a basic condition to form an insulin-gold nanocluster. The technical feature of this method is that the gold precursor is reduced with the insulin, and no additives such as surfactants and reduction agents are added into the reaction mixture. The conventional method for coating gold nanoparticles with proteins is usually performed by forming gold nanoparticles coated with citrate and then substituting ligands on the nanoparticles with proteins. Hence, the conventional method may have the problem that the proteins cannot substitute the ligands on the nanoparticles completely. However, the method of the present invention does not perform the step of ligand substitution, so the problem that the ligands are not completely substituted with insulin can be prevented.

The present invention further provides a pharmaceutical composition for treating diabetes, which comprises: the aforementioned insulin-gold nanocluster, and a pharmaceutically acceptable carrier.

In addition, the present invention also provides a method for detecting adipose cells in a tissue, which comprises: providing the aforementioned insulin-gold nanocluster to a tissue; and examining the fluorescence emitting from the insulin-gold nanocluster to determine whether adipose cells are present in the tissue.

The insulin-gold nanocluster of the present invention is capable of emitting red fluorescence, so it can be applied to various medical fields, such as contract agents for medical imaging technologies, disease detections or evaluations, and insulin-related biological signal detections. In addition, the insulin contained in the insulin-gold nanocluster of the present invention also keeps its own bioactivity and the gold nanocluster has low cytotoxicity, so the insulin-gold nanocluster alone, or the pharmaceutical composition of the present invention, is effective in reducing blood glucose in a subject.

Furthermore, the method for manufacturing the insulin-gold nanocluster is accomplished by directly reducing the gold precursor with the insulin. Hence, the procedure for manufacturing the insulin-gold nanocluster is simple, so the production cost thereof can further be reduced.

In addition, the insulin-gold nanocluster of the present invention can target an insulin receptor, which is expressed in muscle, adipose tissue and liver with high concentration. Hence, the insulin-gold nanocluster of the present invention can be applied to detect the adipose cells in a target tissue, and especially the change of the adipose cells in a target tissue. Furthermore, it is well known that the adipose tissue or adipose cells are highly related to type II diabetes, so the insulin-gold nanocluster of the present invention can also be applied to detecting the risk of suffering from type II diabetes.

In addition, the insulin-gold nanocluster of the present invention also can be applied for insulin-related biological signal detection. For example, a method for detecting an insulin-related biological signal can comprise the following steps: providing detection agents with and without the aforementioned insulin-gold nanocluster respectively to a tissue or a detected subject; examining the fluorescence emitted from the insulin-gold nanocluster in the tissue or the detected subject; and comparing the fluorescence emitted from the tissue or the detected subject treated with the detection agent containing the insulin-gold nanocluster to the fluorescence of that treated with the detection agent without the insulin-gold nanocluster.

According to the insulin-gold nanocluster, the pharmaceutical composition and methods of the present invention, the insulin-gold nanocluster is present in an approximately spherical shape. In addition, the insulin-gold nanocluster emits fluorescence with a quantum yield of at least 6%. Preferably, the insulin-gold nanocluster emits fluorescence with a quantum yield of about 7%.

According to the insulin-gold nanocluster, the pharmaceutical composition and methods of the present invention, the average diameter of the insulin-gold nanocluster may be 0.5-1.2 nm. Preferably, the mean diameter of the insulin-gold nanocluster is 0.5-1.2 nm. More preferably, the mean diameter of the insulin gold nanocluster is 0.8-1.0 nm. Most preferably, the mean diameter of the insulin gold nanocluster is 0.85-0.95 nm.

In addition, according to the insulin-gold nanocluster, the pharmaceutical composition and methods of the present invention, the hydrodynamic radius of the insulin-gold nanocluster may be 2.5-4.5 nm. Preferably, the average hydrodynamic radius of the insulin-gold nanocluster is 2.5-4.5 nm. More preferably, the mean hydrodynamic radius of the insulin-gold nanocluster is 2.5-4.5 nm. Most preferably, the mean hydrodynamic radius of the insulin-gold nanocluster is 3.0-4.0 nm. Herein, the term "hydrodynamic radius" means an effective radius of the insulin-gold nanocluster in a solution measured by assuming that it is a body moving through the solution and resisted by the solution's viscosity.

Furthermore, according to the insulin-gold nanocluster, the pharmaceutical composition and methods of the present invention, the insulin-gold nanocluster emits fluorescence at a wavelength between 620 nm and 690 nm. Preferably, the insulin-gold nanocluster emits fluorescence at a wavelength between 640 nm and 670 nm. More preferably, the insulin-gold nanocluster emits red fluorescence maximized at 670 nm. Since the insulin-gold nanocluster emits red fluorescence maximized at 670 nm, the method for detecting adipose cells in a tissue or the method for detecting insulin-related biological signals may be performed at about 670 nm to obtain more convincing detection results.

In addition, according to the insulin-gold nanocluster, the pharmaceutical composition and methods of the present invention, the insulin-gold nanocluster consists of 10-60% Au. Preferably, the insulin-gold nanocluster consists of 15-40% Au. More preferably, insulin-gold nanocluster consists of 20-30% Au. Most preferably, insulin-gold nanocluster consists of about 25% Au.

The insulin is formed with A-chain and B-chain fragments. In the present invention, the sequence of the A chain fragment is shown as SEQ ID NO 1: GIVEQCCASVCSLYQLENYCN, and the sequence of the B chain fragment is shown as SEQ ID NO 2: FVNQHLCGSHLVEALYLVCGERGFFYTPKA. However, the insulin used in the insulin-gold nanocluster of the present invention is not particularly limited thereto. Any homologous or modified insulin molecules which have a suitable identity or similarity to the aforementioned sequences may be also applied to the insulin-gold nanocluster of the present invention, as long as the homologues of modified insulin molecules still have bioactivity to reduce blood glucose or bind to insulin receptors.

According to the insulin-gold nanocluster, the pharmaceutical composition and methods of the present invention, the insulin may connect to the gold nanocluster through a polar-polar interaction between gold and amino acids of the insulin, since there are only six Cys residues in an insulin molecule, which are all used in the cross S—S linkage of A and B chains in forming insulin. The examples of the amino acids for the polar-polar interaction can be tyrosine, lysine, aspartic acid, arginine, and tryptophan.

According to the method for manufacturing the insulin-gold nanocluster of the present invention, the gold precursor in the reaction mixture may be reduced at pH 9.5-11 to form an insulin-gold nanocluster. Preferably, the gold precursor in the reaction mixture is reduced at pH 10-11. More preferably, the gold precursor in the reaction mixture is reduced at pH 10.2-10.6. In addition, the reaction time and the reaction temperature for performing the reduction are not particularly limited, as long as the insulin can keep its own bioactivity and the insulin-gold nanocluster can be formed. For example, the reaction time is 8-16 hrs. Preferably, the reaction time is 10-14 hrs. More preferably, the reaction time is about 12 hrs. Furthermore, for example, the reaction temperature for performing the reduction may be 0-30° C. Preferably, the reaction time is 0-20° C. More preferably, the reaction time is about 4° C.

In addition, according to the pharmaceutical composition of the present invention, the term "pharmaceutically acceptable carrier" used herein refers to relatively nontoxic chemical compounds or agents that facilitate the incorporation of the active agent (i.e. the insulin-gold nanocluster of the present invention) into cells or tissues. The examples of a pharmaceutically acceptable carrier can be diluents, excipients and solvents.

Furthermore, according to the method for detecting adipose cells in the tissue of the present invention, the tissue can be a tissue from a subject having a risk of type II diabetes. Hence, this method of the present invention can also be applied to evaluate the diabetic risk of a subject who may be at risk to suffer from type II diabetes. When the signal of the insulin-gold nanocluster in the tissue in a normal state is compared to the signal in a diabetic state, the probability or the risk of suffering from diabetes can be determined or evaluated. For example, when the signal of the insulin-gold nanocluster in the detected tissue is higher than that in the tissue in a normal state, it indicates that the detected subject may be at risk to suffer from type II diabetes.

Other objects, advantages, and novel features of the invention will become more apparent from the following detailed description when taken in conjunction with the accompanying drawings.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above explanations. Therefore, it is to be understood that within the scope of the appended claims, the invention may be practiced otherwise than as specifically described.

Embodiment

Preparation of Insulin-Gold Nanocluster

In the present embodiment, bovine pancreas insulin was used, which was purchased from Sigma. The insulin has A-chain and B-chain fragments, wherein the sequence of the A chain fragment was shown as SEQ ID NO 1: GIVEQCCASVCSLYQLENYCN, and the sequence of the B chain fragment was shown as SEQ ID NO 2: FVNQHLCGSHLVEALYLVCGERGFFYTPKA.

The insulin-gold nanoclusters (named as "insulin-Au NCs", hereafter) of the present embodiment were synthesized as follow. First, a reaction mixture was provide, which contained insulin as a soft template and hydrogen tetrachloroaurate(III) trihydrate ($HAuCl_4 \cdot 3H_2O$) in aqueous 0.1 M $Na_3PO_4$ buffer at pH 10.4, 10 mg bovine insulin reacts with 0.1-0.5 mL, 50 mM $HAuCl_4 \cdot 3H_2O$. After the reaction mixture was stirred and reacted 12 hrs in the dark at 4° C., the crude product was purified by centrifugal filtration (4000 g) for 30 min with a cutoff of 5 kDa. Then, red fluorescent insulin Au NCs were obtained.

Insulin-Au NCs Property Examination

Determination of Diameter and Shape of Insulin-Au NCs

The particle size (i.e. the diameter) of insulin-Au NCs were determined by transmission electron microscope (TEM, JEM 1230, JEOL). In addition, high resolution TEM (JEM-2100F, JEOL) examination was also performed, which was operated at 200 kV to determine the shape, the dimension and the size distribution of the obtained insulin-Au NCs. The TEM sample was prepared by drop-casting the insulin-Au NCs on a Cu-grid-supported quantifoil. By observing the casted materials at the hole area of the supporting film, backgroundless image was then obtained.

The high resolution TEM (HRTEM) image of insulin-Au NCs shows that the insulin-Au NCs of the present embodiment have spherical shapes.

Figure 1:
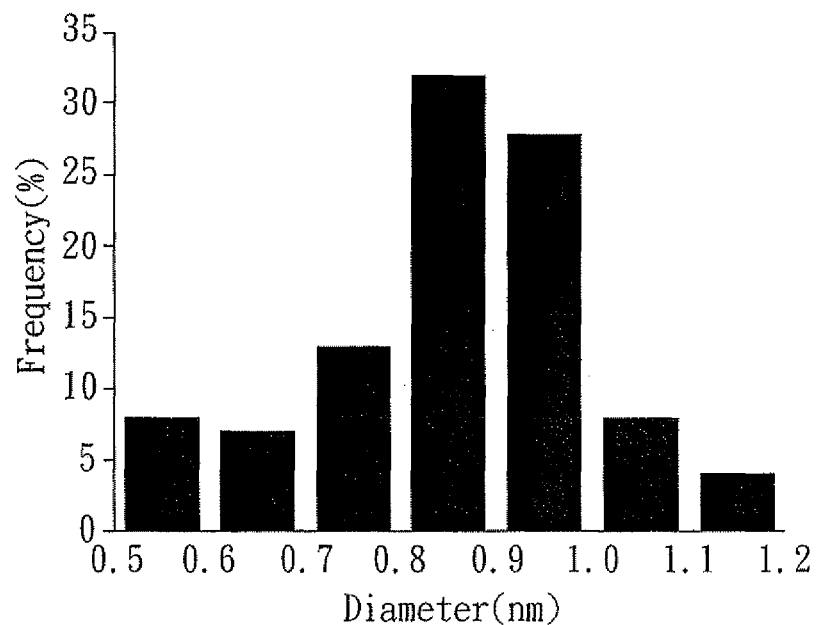
FIG. 1 is a histogram analysis result of insulin-gold nanoclusters according to a preferred embodiment of the present invention.

The histogram analysis of the insulin-Au NCs were constructed based on three TEM photographs and a total of 100 particles were used. The result of the histogram analysis is shown in FIG. 1. As shown in FIG. 1, the insulin-Au NCs of the present embodiment have good size uniformity, and the diameters of the insulin-Au NCs were calculated to be 0.92±0.03 nm. In addition, the hydrodynamic radii of the insulin-Au NCs were also measured by dynamic light scattering, which gave diameters of 3.5±0.4 nm.

Determination of Absorption and Emission Spectra of Insulin-Au NCs

The absorption and photoluminescence emission spectra of the insulin-Au NCs of the present embodiment were examined with Hitachi U-3310 spectrophotometer and Edinburgh FS920 fluorimeter respectively. The insulin-Au NCs were suspended and the spectra of the aqueous solution of the insulin-Au NCs were determined. The spectral responses of excitation and emission of the fluorimeter were both calibrated. In addition, the emission quantum yield of insulin-Au NCs was determined by comparison method, in which a DCM dye (4-(Dicyanomethylene)-2-methyl-6-(4-dimethylaminostyryl)-4H-pyran) solution in methanol with known quantum yield of about 0.44 served as a standard.

Figure 2:
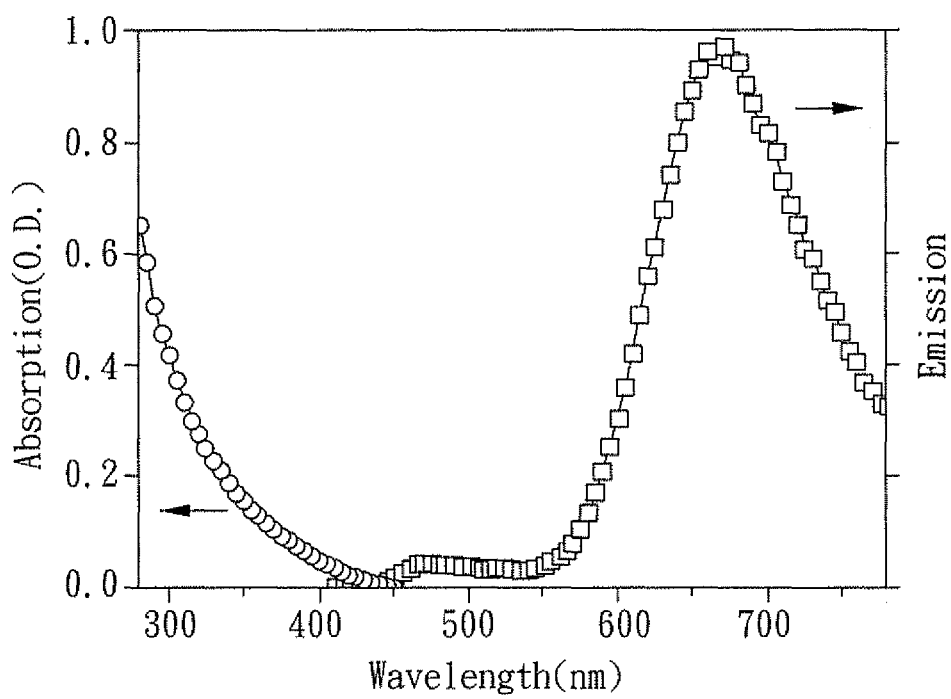
FIG. 2 is absorption and photoluminescence emission spectra of insulin-gold nanoclusters according to a preferred embodiment of the present invention.

The results of the absorption and photoluminescence emission spectra of the insulin-Au NCs are shown in FIG. 2. As show in FIG. 2, the excitation wavelength of the insulin-Au NCs is about 400 nm, and the emission wavelength thereof is about 670 nm. In addition, after the comparison method was performed to determine the emission quantum yield of the insulin-Au NCs, the result showed that the emission quantum yield was determined to be 0.07 (i.e. 7%).

Determination of Composition of Insulin-Au NCs

Energy-dispersive X-ray (EDX) spectrometry was used to determine Au composition in the insulin-Au NCs, and X-ray photoelectron spectrometry (XPS/ESCA) was used to determine the in-depth chemical state of the insulin-Au NC. Herein, the EDX samples were prepared by drop-casting insulin-Au NCs on a carbon-coated copper mesh grid, and the XPS samples were prepared by drop-casting insulin-Au NCs on a Si wafer, and the spectra were recorded with a PHI 5000 VersaProbe scanning ESCA microprobe (ULVAC-PHI, Japan) using a micro-focused, monochromatic Al Kα X-ray (25 W, 100 µm). The take-off angle of the photoelectron was 45°. A dual beam charge neutralizer ($Ar^+$ gun and flooding electron beam) was used to compensate for the charge up effect.

The best fit of the data from X-ray spectrometry indicated that insulin-Au NCs consisted of approximately 24.3% Au and complementary metallic Au.

Determination of Cytotoxicity of Insulin-Au NCs

The cytotoxicity of the insulin-Au NCs was detected through MTT assay, wherein C2C12 and 3T3-L1, a mouse myoblast cell line and a mouse embryonic fibroblast cell line (adipose like cell lines) were used as a test candidate.

First, cells were seeded in a 24-well plate with a density of $3 \times 10^4$ cells per well in 1 mL serum-free DMEM (Dulbecco's modified Eagle's medium, GIBCO) culture medium. Then, five different dosages of the insulin-Au NCs were added to each of the cell samples: 250, 200, 150, 100, 50, and 0 µg/mL. After 24 hrs of incubation, each well was washed twice with phosphate-buffered saline (PBS, 137 mM NaCl, 2.68 mM KCl, 10 mM $Na_2HPO_4$, 1.76 mM $KH_2PO_4$, pH 7.4), and replenished with 500 µL culture medium with 10% of MTT (3-(4,5-dimethylthiazol-2-yl)-2,5-diphenyltetrazolium bromide) agent (Roche). After 3 hrs of incubation and medium removal, the newly formed purple MTT-formazan was dissolved in 300 µL dimethyl sulfoxide (Sigma-Aldrich) and the absorbance was measured at 595 nm with fluorescence (BIO-RAD model 680).

Figure 3:
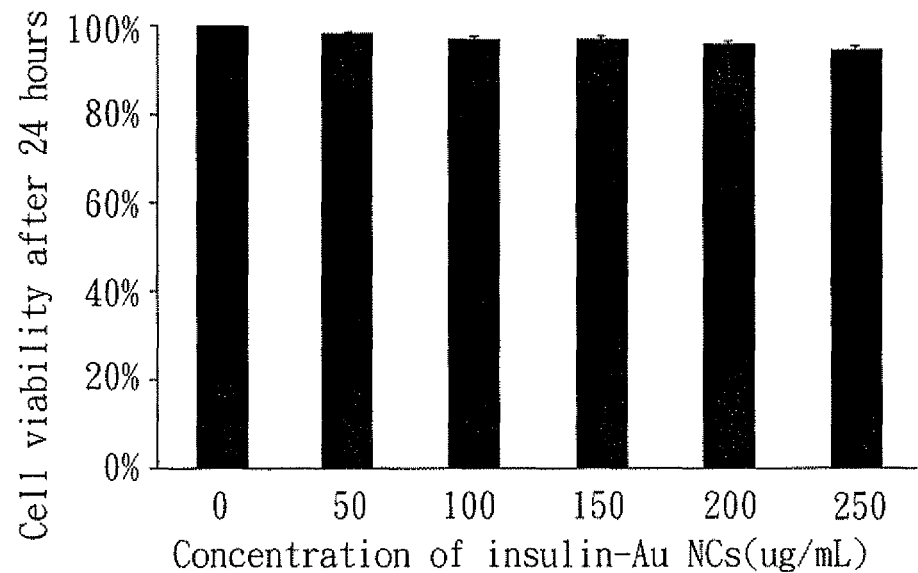
FIG. 3 is a result of MTT assay showing the cytotoxicity of insulin-gold nanoclusters to C2C12 cells according to a preferred embodiment of the present invention.
Figure 4:
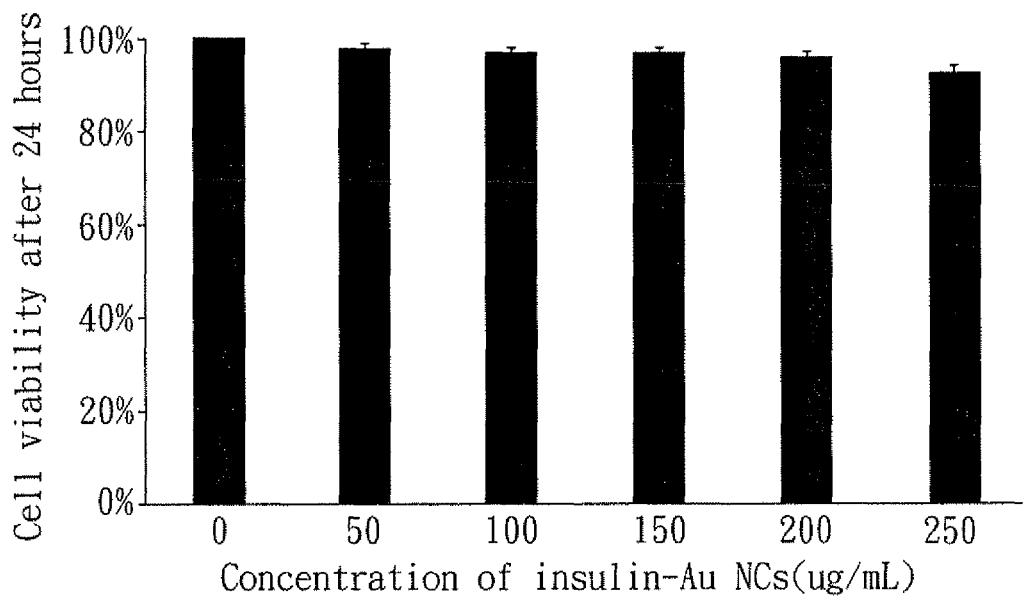
FIG. 4 is a result of MTT assay showing the cytotoxicity of insulin-gold nanoclusters to 3T3-L1 cells according to a preferred embodiment of the present invention.

FIG. 3 and FIG. 4 show the result of the MTT assay for evaluating the viability of C2C12 myoblast cells or 3T3-L1 cells treated with the insulin-Au NCs, respectively. As shown in FIG. 3, even though the dosage of the insulin-Au NCs was up to 250 µg/mL, the C2C12 myoblast cells still showed high cell viability. In addition, as shown in FIG. 4, the 3T3-L1 cells also still showed high cell viability. This result indicates that the insulin-Au NCs of the present embodiment have low cytotoxicity and superior biocompatibility. Therefore, when the insulin-Au NCs of the present embodiment are applied to medical use, the insulin-Au NCs can bind or target insulin receptors without causing cell death.

Insulin-Au NCs Stability Evaluation

Figure 5:
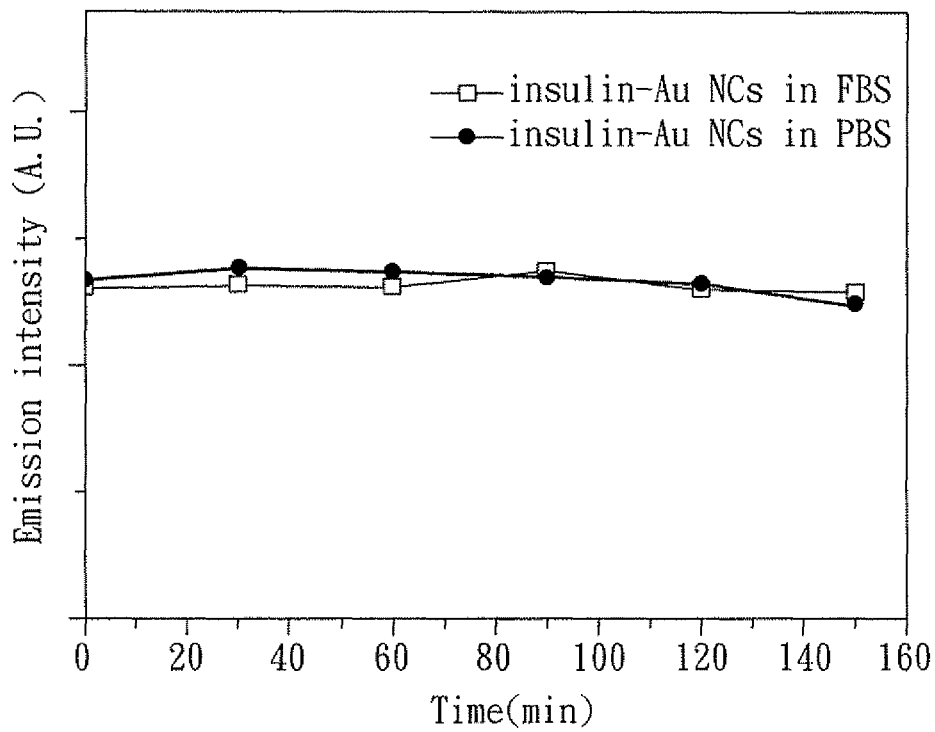
FIG. 5 is a result showing the stability of insulin-gold nanoclusters according to a preferred embodiment of the present invention.

The insulin-Au NCs were placed in a PBS buffer and a complex matrix to evaluate the stability thereof, wherein the complex matrix was fetal bovine serum (FBS), which contains various growth factors and proteins including BSA, globulins, and fibrinogen. The stability of the insulin-Au NCs was determined according to the fluorescence intensity emitting therefrom, wherein the fluorescence intensity was determined with Edinburgh FS920 fluorimeter, and the result is shown in FIG. 5, wherein the y-axis is asymmetric unit (A.U.). As shown in FIG. 5, the fluorescence intensity emitting from the insulin-Au NCs of the present embodiment did not change a lot, whether the insulin-Au NCs were kept in a simple buffer (PBS) or a complex matrix (FBS). In addition, the fluorescence intensity emitting from the insulin-Au NCs of the present embodiment also did not change a lot, even though the insulin-Au NCs were stored for 2 hrs. These results indicate that insulin-Au NCs of the present embodiment have goods stability.

Evaluation of Internalization Between Insulin-Au NCs and Cells

First, C2C12 myoblast cells or 3T3-L1 cells were seeded in a 6 well plate at $3 \times 10^4$ cell/well density in 2 mL of serum-free culture medium. Next, 250 μg/mL of the insulin-Au NCs were added into each well. After the insulin-Au NCs were incubated with cells for an appropriate incubation time, the cells were washed three times with PBS and then fixed in a 3.7% paraformaldehyde in PBS at room temperature for 10 min. Then, the cells were washed with PBS twice, and incubated with 0.1% Triton X-100 (Sigma-Aldrich) in PBS at room temperature for 5 min.

Here, laser-scanning confocal fluorescence microscopy was used for examining the cellular uptake of the insulin-Au NCs. 4',6-diamidino-2-phenylindole (DAPI, Molecular Probes) and Alexa Fluor® 488 phalloidin were used in this optical microscopic study for nucleus and actin labeling, respectively. After the cells were completely washed with PBS twice, the cells were stained with 10 μg/mL DAPI in PBS for 5 min at room temperature. The stained cells were washed twice with PBS and then examined by a Zeiss LSM710 NLO confocal spectral microscope equipped with 63× (P-APO, 1.40 Oil immersion) objective, and using 405 nm Diode laser, 488 nm Argon laser, and 543 nm He—Ne laser as excitation source.

When the insulin-Au NCs were incubated with C2C12 cells for 2 hrs, the confocal image (not shown in the figures) showed that the intense red fluorescence of the insulin-Au NC overlaps with that of the fully differentiated C2C12 cells in the cytoplasma. These results show that the uptake efficiency of the insulin-Au NCs for C2C12 cells may serve as a biomarker to distinguish the differentiated versus undifferentiated C2C12 myoblast cells.

When the insulin-Au NCs were incubated with 3T3-L1 cells for 2 hrs, the confocal image (not shown in the figures) showed that the intense red fluorescence of the insulin-Au NC can be observed in 3T3-L1 cells. This result indicates that the insulin-Au NCs of the present embodiment can be used as a biomarker for detecting the adipose cells.

In addition, a detailed two-photon z-stacking study was also performed to identify the internalization of the insulin-Au NCs. The confocal image (not shown in the figures) showed that the insulin-Au NCs entered into the cells and were distributed in the cytoplasma, and the insulin-Au NC uptake by the undifferentiated C2C12 cells was much smaller.

These results indicate that the insulin-Au NCs of the present embodiment can bind to insulin receptors and enter into the cytoplasma through the insulin receptors. Hence, the insulin-Au NCs of the present embodiment can serve as a biomarker to detect insulin-related biological signals.

Identification of Contrast Enhancement of Insulin-Au NCs

For evaluation of the contrast enhancement of the insulin-Au NCs of the present embodiment, 0, 1, 3, 10, and 30 mg/mL of the insulin-Au NCs were placed in eppendorf tubes for X-ray compouted tomography (CT), and the CT instrument used herein is Sixty-four Multislice CT (Lightspeed VCT, GE Healthcare, USA). The eppendorf tubes were positioned in a home-made rack to perform the CT imagaing. The rack was scanned 4 times under 80 keV, 100 mA at the field of view (FOV) of 32 cm. The resolution was 512×512 and the slice thickness was 0.625 mm. Under this condition, a voxel is $0.625 \times 0.625 \times 0.625$ cm$^3$, which is isotropic. The CT numbers of each eppendorf tube were measured at the workstation provided by the vendor of the CT (Advantage Workstation AW 4.2_07, GE healthcare, USA).

The result shows that the Au NCs in the insulin-Au NCs induced a contrast enhancement in a dose-dependent manner (not shown in the figures).

In addition, the differentiated C2C12 myoblast cells were also treated with the insulin-Au NCs, and then purified to examine with CT imaging. The result shows that the insulin-Au NCs encapsulated in the C212 cells can exhibit apparent CT enhancement (not shown in the figures).

These results indicate that the insulin-Au NCs of the present embodiment can not only emit red fluorescence but also show strong CT signal elevation. Hence, the insulin-Au NCs of the present embodiment have potential as a two-in-one agent, that is, for fluorescence imaging and CT imaging.

Insulin-Au NCs Bioactivity Evaluation

Ten-week-old C57BL/6J male mice were purchased from the Animal Center of National Cheng Kung University Medical College. The mice were housed in a temperature-(25±1° C.) and humidity-(60±5%) controlled room and kept on a 12:12 light-dark cycle (light on at 06:00 AM).

First, the mice were fasted for 6 h and then anesthetized intraperitoneally (i.p.) with 75 mg/kg of pentobarbital (Sigma-Aldrich). The mice were i.p. administered with 1.0 unit/kg Humulin R (Eli Lilly) or the insulin-Au NCs of the present embodiment, and then the blood samples were collected from the retro-orbital sinus of each mouse at 0, 30, 60, 90, and 120 min for blood glucose measurements. The blood samples were centrifuged at 9,000×g for 3 min and the serum was collected for blood glucose determination by an automatic blood glucose meter (Quik-Lab, Ames; Miles Inc.). The results are shown in FIG. 6.

Figure 6:
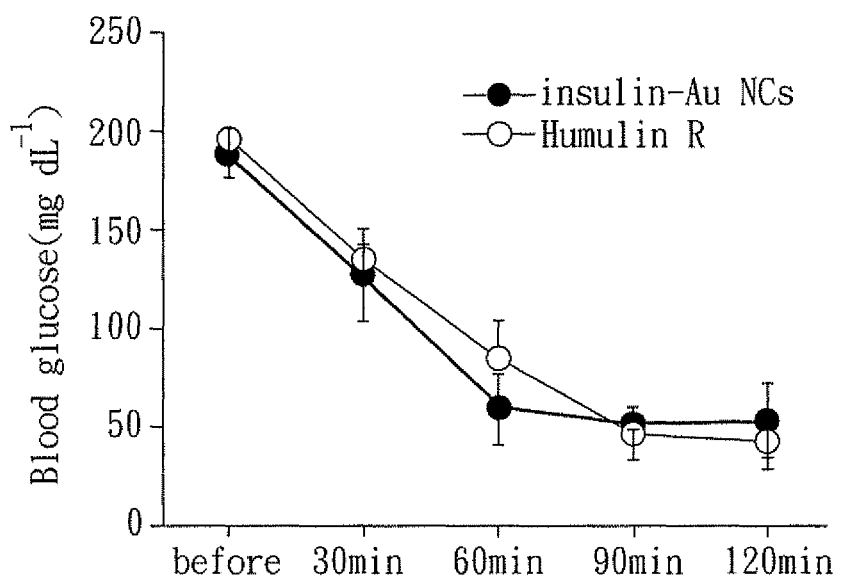
FIG. 6 is a result showing the bioactivity of insulin-gold nanoclusters according to a preferred embodiment of the present invention.

As shown in FIG. 6, under the same dosage of 1.0 unit/kg, an intraperitoneal (i.p.) injection of the insulin-Au NCs into mice rendered a trend of reducing the blood glucose similar to that of commercial insulin (Humulin R). Hence, the insulin contained in the insulin-Au NCs of the present embodiment still keeps its bioactivity for reducing blood glucose. Therefore, the insulin-Au NCs of the present embodiment can be applied to the medical use for reducing or regulating blood glucose and treating diabetes.

In addition, ten-week-old C57BL/6J male mice were well-anesthetized by i.p. injection of pentobarbital (75 mg/kg), and then the brain was removed and homogenated in PBS. The homogenate was then centrifuged at 6,000×g for 20 min and the supernatant was collected for the preparation of further experiments.

0.01, 0.1, and 1 mM doses of thiorphan or racecadotril, which was known as inhibiting agents for insulin-degradation enzyme (IDE), were co-incubated with the brain homogenates for 30 min, and then 10 μg/ml insulin-Au NCs was added and incubated with brain homogenates for 1 hour at 37° C. The detection of the insulin-Au NCs was determined by 450 nm and 650 nm of the emission excitation wavelength, respectively. The results are shown in FIG. 7.

Figure 7:
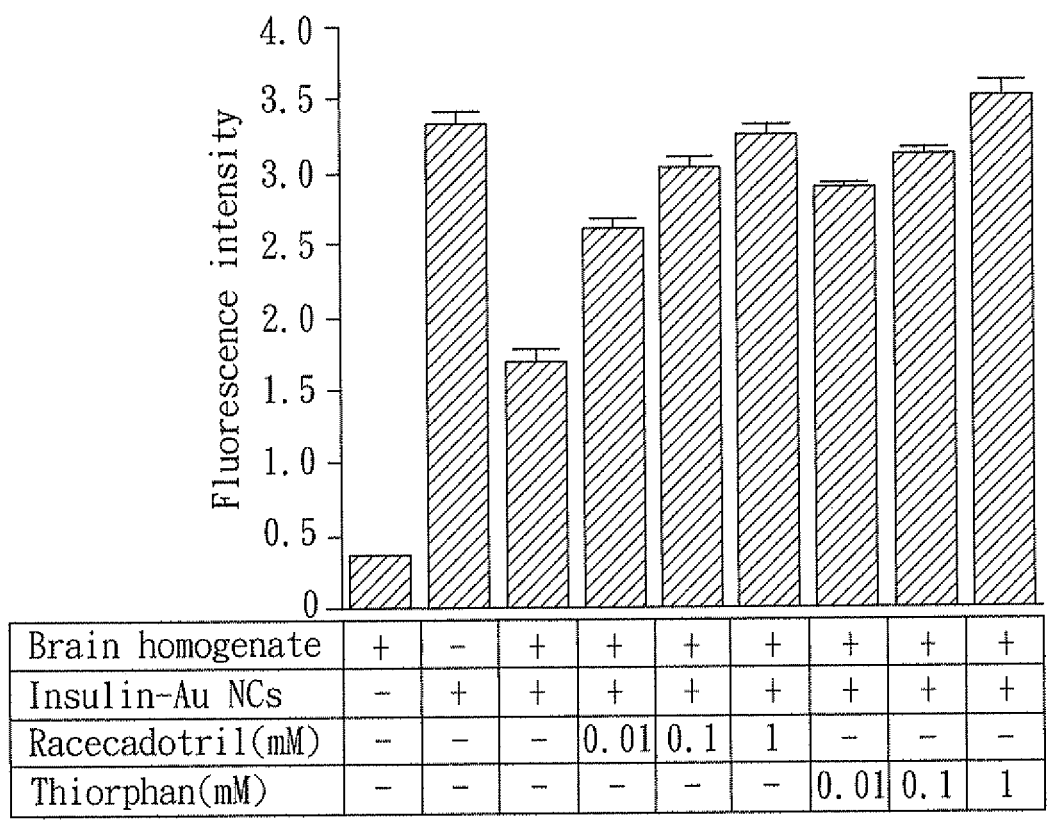
FIG. 7 is a result showing the interaction between insulin-degrading enzyme and insulin-gold nanoclusters according to a preferred embodiment of the present invention.

As shown in FIG. 7, when the insulin-Au NCs of the present embodiment was added into the brain homogenate, a significant quenching (ca. 50%) of the Au NC emission at 670 nm was observed. This result indicates that the insulin-Au NCs can be degraded by IDE, which may lead to the release of Au NCs and result in quenching of the emission.

In addition, the 670 nm emission intensity was regained and signal recovery was increased upon increasing the racecadotril or thiorphan dosage from 0.01 to 1 mM. This result indicates that both racecadotril and thiorphan can inhibit IDE and prevent the insulin degradation on the insulin-Au NCs of the present embodiment.

According to the results shown in FIG. 7, it can be found that the insulin-Au NCs of the present embodiment can be applied to use for detecting cell insulin-related biological signals.

Although the present invention has been explained in relation to its preferred embodiment, it is to be understood that many other possible modifications and variations can be made without departing from the spirit and scope of the invention as hereinafter claimed.

What is claimed is:

1. An insulin-gold nanocluster, comprising:

a gold nanocluster; and insulin connecting to the gold nanocluster, wherein the insulin-gold nanocluster is spherical, has a diameter of 0.5-1.2 nm and a hydrodynamic radius of 2.5-4.5 nm, and emits fluorescence at a wavelength between 620 nm and 690 nm with a quantum yield of at least 6%.

2. The insulin-gold nanocluster as claimed in claim 1, wherein the insulin connects to the gold nanocluster through a polar-polar interaction between gold and amino acids of the insulin.

3. A pharmaceutical composition for reducing blood glucose, comprising:

an insulin-gold nanocluster, which comprises: a gold nanocluster; and insulin connecting to the gold nanocluster, wherein the insulin-gold nanocluster is spherical, has a diameter of 0.5-1.2 nm and a hydrodynamic radius of 2.5-4.5 nm, and emits fluorescence at a wavelength between 620 nm and 690 nm a with a quantum yield of at least 6%; and a pharmaceutically acceptable carrier.

4. The pharmaceutical composition as claimed in claim 3, wherein the insulin connects to the gold nanocluster through a polar-polar interaction between gold and amino acids of the insulin.

5. The pharmaceutical composition as claimed in claim 3, wherein the pharmaceutical composition is applied to a subject having diabetes to reduce the blood glucose in the subject.

6. A method for detecting adipose cells in a tissue, comprising:

providing the insulin-gold nanoclusters of claim 1 to a tissue; and examining the fluorescence emitting from the insulin-gold nanoclusters to determine whether adipose cells are present in the tissue.

7. The method as claimed in claim 6, wherein the tissue is a tissue from a subject having a risk of type II diabetes.

8. The method as claimed in claim 6, wherein the insulin connects to the gold nanocluster through a polar-polar interaction between gold and amino acids of the insulin.

9. The insulin-gold nanocluster as claimed in claim 1, wherein the insulin is whole insulin comprising an A-chain fragment and a B-chain fragment.

10. The pharmaceutical composition as claimed in claim 3, wherein the insulin is whole insulin comprising an A-chain fragment and a B-chain fragment.

* * * * *

SEQUENCE LISTING

```
<160> NUMBER OF SEQ ID NOS: 2

<210> SEQ ID NO 1
<211> LENGTH: 21
<212> TYPE: PRT
<213> ORGANISM: Bos primigenius

<400> SEQUENCE: 1

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Bos primigenius

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30
```